United States Patent [19]

Coates et al.

[11] 4,195,916

[45] Apr. 1, 1980

[54] LIQUID CRYSTAL COMPOUNDS

[75] Inventors: David Coates, Bishops Stortford; George W. Gray, Cottingham; Damien G. McDonnell, Hull, all of England

[73] Assignee: The Secretary of State for Defence in Her Britannic Majesty's Government of the United Kingdom of Great Britain and Northern Ireland, London, England

[21] Appl. No.: 893,611

[22] Filed: Apr. 5, 1978

[30] Foreign Application Priority Data

Apr. 5, 1977 [GB] United Kingdom ............ 14296/77

[51] Int. Cl.² ............ C07C 69/74; C07C 69/78; C09K 3/34; G02F 1/13; G01K 11/16; C07C 69/63; C07C 69/65; C07C 69/90
[52] U.S. Cl. ............ 350/346; 73/356; 252/408; 252/299; 350/350; 428/1; 560/1; 560/59; 560/62; 560/64; 560/65; 560/66; 560/73; 560/102; 560/106; 560/107; 560/108; 560/111
[58] Field of Search ............ 252/299, 408; 350/350, 350/346; 560/59.66, 73, 65, 102, 62, 108, 111, 1, 64, 106, 107; 73/356; 428/1

[56] References Cited

U.S. PATENT DOCUMENTS

| | | | |
|---|---|---|---|
| 3,891,307 | 6/1975 | Tsukamoto et al. | 350/350 |
| 3,915,883 | 10/1975 | Van Meter et al. | 252/408 |
| 3,947,375 | 3/1976 | Gray et al. | 252/299 |
| 4,002,670 | 11/1977 | Steinstrasser | 252/299 |
| 4,065,489 | 12/1977 | Steinstrasser et al. | 252/299 |
| 4,077,260 | 3/1978 | Gray et al. | 252/299 |
| 4,082,428 | 4/1978 | Hsu | 252/299 |
| 4,083,797 | 4/1978 | Oh | 252/299 |
| 4,105,654 | 8/1978 | Bloom et al. | 252/299 |
| 4,149,413 | 4/1979 | Gray et al. | 252/299 |

FOREIGN PATENT DOCUMENTS

105701 5/1974 German Democratic Rep. ..... 252/299

OTHER PUBLICATIONS

Klanderman, B. H., et al., J. Am. Chem. Soc., vol. 97, No. 6, pp. 1585–1586 (1975).
Goodby, J. W. et al., Mol. Cryst. Liq. Cryst. (Lett.), vol. 34, pp. 183–188 (1977).
Gray, G. W. et al., Mol. Cryst. Liq. Cryst. (Lett.), vol. 34, pp. 211–217 (1977).
Gray, G. W. et al., Mol. Cryst. Liq. Cryst., vol. 37, pp. 189–211 (1976).
Goodby, J. W. et al., "Some Effects of Small Changes in Molecular Framework on the Incidence of Smectic C and Other Smectic L.C. Phases in Esters," Abst. I-6, 6th Int. L.C. Conf. Kent, Ohio (1976).

*Primary Examiner*—Teddy S. Gron
*Attorney, Agent, or Firm*—Stevens, Davis, Miller & Mosher

[57] ABSTRACT

Novel liquid crystal compounds are disclosed, which are chiral esters based upon the phenol

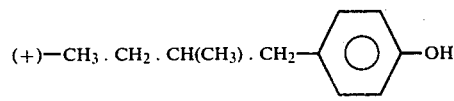

Typical examples are:

(+) . CH₃ . CH₂ . CH(CH₃) .

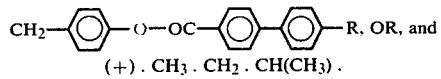

(+) . CH₃ . CH₂ . CH(CH₃) .

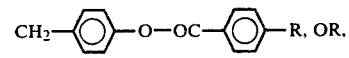

and mixtures of these compounds have a helical pitch such that the mixtures reflect light of a specific wavelength when illuminated with ordinary light and the pitch is temperature sensitive so that the mixtures can be used in temperature indicating devices. Specific examples are given as are samples of mixtures that can be used in phase change electro-optic display devices.

12 Claims, No Drawings

LIQUID CRYSTAL COMPOUNDS

The present invention is concerned with optically active phenol esters which display liquid crystal phases, and with electro-optical display devices containing them either on their own or in admixture with other compounds.

Liquid crystal phases are exhibited by certain organic compounds and constitute an intermediate state which exists between the crystalline solid and the fully disordered liquid phase and within which certain long range ordering of the molecules takes place.

There are two broad types of liquid crystal phase; the smectic mesophase in which the long range ordering is of a substantially lamellar type and the nematic mesophase in which the ordering is substantially linear, ie the molecules tend to line up with the long axes of the molecules parallel. Included sometimes as a sub-class of the nematic mesophase and sometimes classified as a separate mesophase is the cholesteric mesophase. This last has a helical long range order imposed upon the linear order of the nematic mesophase. Compounds displaying a cholesteric mesophase are optically active (chiral) and the pitch of the helical twist is determined by the nature and extent of the optical activity.

Optically active liquid crystal materials, or mixtures, find use in electrooptical devices of the cholesteric-to-nematic phase change kind, or in applications where the colour of the cholesteric mixture can change either with temperature (thermochromic applications—eg, surface thermography, temperature detection) or with the presence of an impurity (applications to detect unwanted particles, liquids or vapours, eg, atmospheric pollutants).

In accordance with the present invention a liquid crystal compound is an ester having the formula:

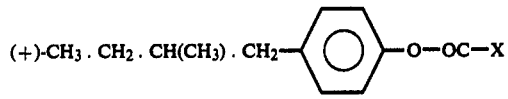

Where X is selected from the following groups:

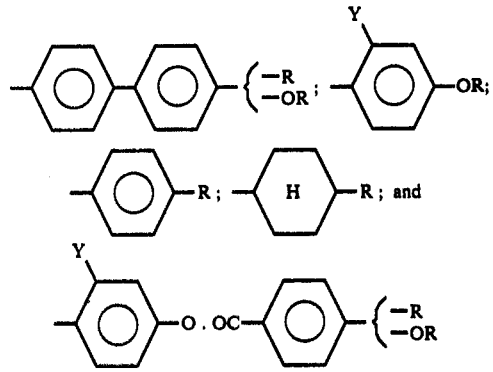

where R is a normal or branched chain alkyl group, which may be chiral, preferably having less than fifteen carbon atoms, and where Y is a halogen (preferably chlorine), a methyl group, or a hydrogen atom.

These compounds exhibit, either on their own or as mixtures with other suitable materials, a cholesteric phase (hereinafter designated Ch) because of their molecular shape and optical activity. The molecules are arranged in a helical formation such that a film of the phase in the Grandjean plane texture rotates the plane of polarisation of incident polarised light, and reflects elliptically polarised light of specific wavelengths when illuminated by ordinary light; such cholesteric mesophases are thermochromic if the light reflected is in the visible range and the pitch is sensitive to temperature change.

The compounds of the present invention have properties such that they may be used in a liquid crystal electro-optic device such as a 'phase change' device in which the material is changed between a so-called 'focal-conic' cholesteric state, which scatters light, and a transparent nematic state, by an applied electric field. In accordance with one aspect of the present invention, an electro-optic device includes as its liquid crystalline material a compound as hereinbefore defined, but it will of course be realised that there may be present a mixture (solution) of compounds as hereinbefore defined and also that other compounds possibly exhibiting liquid crystalline behaviour may be included. Preferably when a mixture of compounds is used that mixture is a eutectic. The optical effect of the electro-optical device may be enhanced by the inclusion of pleochroic dyes. Suitable pleochroic dyes for this purpose are described in copending UK patent applications numbered 25843/75 and 25859/75.

The cholesteric phases of the materials of the present invention, or their mixtures with one another or with other suitable materials, may exhibit thermochromism. It is believed that this occurs because the helical pitch lengths of the molecular formations are such as to give strongly temperature dependent Bragg reflection of particular wavelengths of light in the visible spectral region. That is the materials appear coloured with a colour which varies with the temperature of the material. The materials of the present invention may thus be used in surface thermography, eg for the detection of breast cancer, and in accordance with a further aspect of the present invention a temperature display device includes as its temperature sensitive material a liquid crystal material as defined or a mixture of such material with a suitable material.

The present invention will now be described by way of example only with reference to the following examples which illustrate typical synthetic routes for the preparation of materials in accordance with the present invention, and which describe the physical properties of typical liquid crystal materials in accordance with the present invention.

In the examples the following symbols have the meaning assigned to them below:

(+): which refers to an optically active material whose isotropic solutions have a positive optical rotation angle.

(−): Which refers to an optically active material whose isotropic solutions have a negative optical rotation angle.

$[\alpha]_D^{20}$: which is an absolute measure of the rotary power (specific rotation) of an optically active material when forming a 10% w/v solution in chloroform at 20° C.

and phases are indicated as below

C—Crystal
$S_A$—Smectic A
$S_B$—Smectic B
$S_C$—Smectic C

Ch—Cholesteric
N—Nematic
I—Isotropic liquid
( )—Brackets around a temperature indicate a monotropic transition, which is not observable during a heating cycle, but may be observed on cooling.
Phase changes are indicated thus:
C—S$_A$—Crystal to Smectic A, for example. Temperatures are given in °C.

The optically active compounds described below have a positive optical rotation angle denoted by the symbol (+). Analogous compounds with negative optical rotation angles (−) or racemic compounds (±) may be prepared by analogous routes using the appropriate or racemic reactants in the preparation routes.

EXAMPLE 1

The production of (+)-4-(2′-methylbutyl)phenol by the following route:

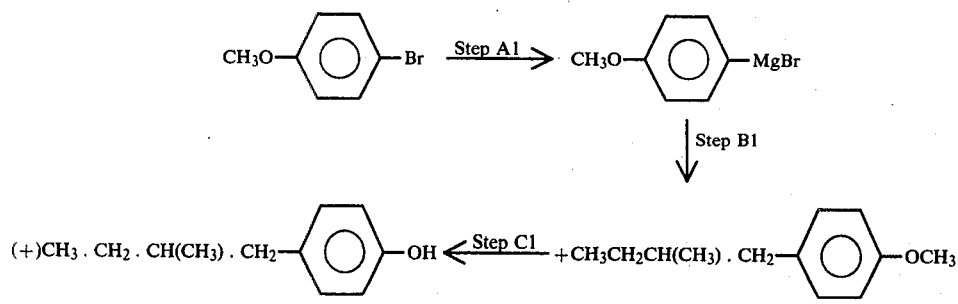

Step A1

The production of 4-methoxyphenyl-1-magnesium bromide.

Under anhydrous conditions, 4-bromoanisole (0.49 mole) in sodium dry ether (250 ml) is added to magnesium turnings (0.5 g atom) covered with sodium dry ether (100 ml). A small volume (30 ml) of the solution is added to the magnesium and a single crystal of iodine is used to initiate the reaction. Once the reaction has begun, the remaining solution of 4-bromoanisole is added in drops so as to maintain the reaction at a steady rate. When addition is complete the reaction mixture is heated under reflux and stirred for one hour.

Step B1:

The production of (+)-4-(2′-methylbutyl)-1-methoxybenzene.

The solution of Grignard reagent from 4-bromoanisole is cooled in an ice bath and a solution of iron(III) chloride (0.05 mole) in ether (5 ml) is added dropwise, followed immediately by a solution of (+)-2-methylbutyl bromide (0.49 mole), in sodium dry ether (100 ml). The mixture is then left to stir at room temperature for 24 hr, and finally heated under reflux for 12 hr.

On cooling, the mixture is poured into a 10% hydrochloric acid solution (1500 ml) at 0° C. and stirred for 1 hr. The product is extracted into ether (3×200 ml) and the combined ether extracts are washed with water (3×200 ml) and dried (Na$_2$SO$_4$). The ether is evaporated off and the oily residue distilled, collecting the fraction boiling between 205°–212° C. at 400 mm Hg.

(+)-2′-methylbutyl bromide is prepared as follows:

To a stirred solution of commercially available (−)-2-methylbutanol (0.34 mole) in dry 'Analar' (Trade Mark) pyridine (0.12 mole) is added in drops phosphorus tribromide (0.136 mole). The temperature during the addition is maintained below 15° C. by cooling the mixture in an ice bath. The white emulsion which forms is stirred at room temperature for 2 hours. After this time the crude bromide is distilled from the emulsion under reduced pressure (300 mm Hg) until the mixture turns orange and 'seeths'.

The crude distillate is taken up in petroleum ether (b.p. 40°/60° C.; 100 ml) and is washed with:
(a) 5% sodium hydroxide solution (3×50 ml);
(b) water (3×50 ml);
(c) 10% sulphuric acid (2×50 ml);
(d) concentrated sulphuric acid (100 ml);
(e) water (2×100 ml).

The solution is dried over anhydrous sodium sulphate and the solvent is then evaporated off. The residue is distilled and the fraction boiling at 121° C. collected (96.5% pure by g.l.c.). The product has $[\alpha]_D^{20}$ 3.9°.

Step C1:

The production of (+)-4-(2′methylbutyl)phenol.

(+)-4-(2′-methylbutyl)-1-methoxybenzene (0.12 mole) constant boiling hydrogen bromide in water (96 ml) and 45% w/v hydrogen bromide in acetic acid (140 ml) are heated under reflux for 6 hr.

On cooling, the mixture is poured into water (1000 ml) and stirred for 0.5 hr. The product is extracted into ether and the combined extracts washed with water and dried (Na$_2$SO$_4$). The ether is rotary evaporated off and the residue distilled at 0.1 mm Hg at an oil bath temperature of 160° C. and is found to be 99.2% pure by g.l.c.

Preparation and Availability of 4-alkyl and 4-alkyloxybiphenyl-4′carboxylic acids, both straight chain and branched 4-n-alkyl- and 4-n-alkyloxybiphenyl-4′-carboxylic acids are prepared by hydrolysis of the corresponding cyano compounds, which are commercially available, and of which the preparations have been described, for example, in UK Patent No. 1,433,130.

The preparation of 4-n-octylbiphenyl-4′carboxylic acid is given in Example 2 by way of example.

EXAMPLE 2

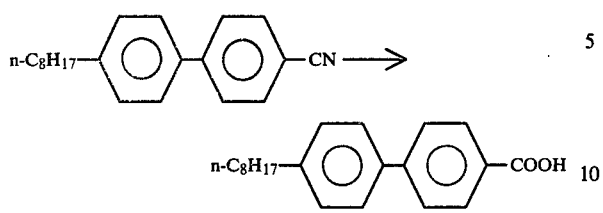

4-n-Octyl-4'-cyanobiphenyl (0.015 mole) is dissolved in methanol (50 ml) and the solution added to a mixture of potassium hydroxide (0.54 mole) and sodium hydroxide (0.75 mole) in methanol (40 ml) and water (20 ml). The mixture is heated under reflux until the evolution of ammonia ceases. Then the mixture is diluted with water (100 ml) and acidified with concentrated hydrochloric acid. The acidified mixture is heated to 80° C. for 2 hr, cooled, and the acid product is filtered off and crystallised twice from ethanol.

The product has the following constants:
C—$S_C$, 150° C.; $S_C$—N, 238.5° C.; N—I, 242.6° C.

(+)-4-Branched-alkyl- and -alkyloxy-biphenyl-4-carboxylic acids can be prepared by the same route of hydrolysing the corresponding cyano-compounds. Alternatively the (+)-4-branched-alkyloxybiphenyl-4'-carboxylic acid can be obtained from the corresponding (+)-4-branched-alkyloxybiphenyl by a Fridel-Crafts acylation to introduce a —CO.$CH_3$ group into the 4'-position in the biphenyl ring followed by its oxidation to a carboxylic acid group.

Preparation and Availability of the required 4-substituted benzoic acids.

4-Alkylbenzoic acids are either commercially available or may be prepared by standard synthetic methods such as the acetylation of commercially available alkylbenzenes (Friedel-Crafts Acetylation) followed by hypobromite oxidation of the 4-alkylacetophenone to the corresponding acid as described by Gray and Brynmor Jones, J Chem Soc., 1954, 678.

4-Alkyloxybenzoic acids may be readily prepared. One way of preparing these materials is by the standard method of alkylating hydroxy aromatic carboxylic acids described by Gray and Brynmor Jones, J Chem Soc, 1954 678; in this case the starting material is 4-hydroxybenzoic acid.

Substituted 4-alkyloxybenzoic acid may be prepared by standard synthetic routes.

2-Chloro-4-alkyloxybenzoic acids may be prepared by the following route:

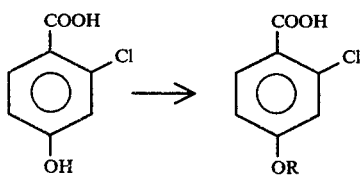

using the standard method described by Gray and Brynmor Jones J Chem Soc, 1954,678 and using commercially available 2-chloro-4-hydroxybenzoic acid as starting material.

2-Methyl-4-alkyloxybenzoic acids may be prepared by the following route as set out in Example 3 below:

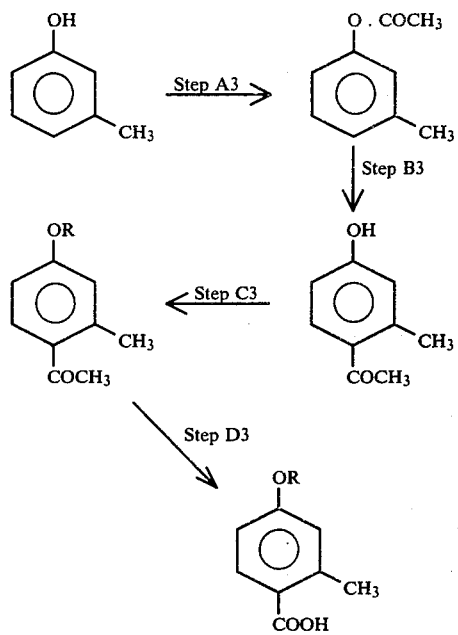

EXAMPLE 3

Step A3

3-methylphenyl acetate may be prepared by the standard acetylation of m-cresol as described in 'Practical Organic Chemistry' by AI Vogel, Longmans Green and Co London, 3rd edition, p. 699. The product boils at 210° C.

Step B3

4-hydroxy-2-methylacetophenone may be produced by the standard Fries Rearrangement of aryl alkanoates described in 'Organic Reactions', Vol 1 (Editor in Chief: R Adams), John Wiley & Sons Inc., NY, P 354. The product has mp 130° C.

Step C3

4-alkyloxy-2-methylacetophenones may be produced by the well known method of heating a solution of the 4-hydroxy-2-methylacetophenone (1 mole) and the alkyl bromide (1.2 mole) in cyclohexanone, together with solid, anhydrous potassium carbonate (4–5 moles). The mixture is heated and stirred for 4–5 hr. It is then filtered to remove inorganic material, which is washed with a solvent such as ether. The combined filtrate and ethereal washings are distilled to remove the solvents. The residue is then distilled under reduced pressure to yield the pure 4-alkyloxy-2-methylacetophenone.

Step D3

2-methyl-4-alkyloxybenzoic acids may be produced by the standard method of oxidation of the acetyl group using sodium hypobromite solution as described by Gray & Brynmor Jones (J Chem Soc, 1954, 678). After treatment of the methyl ketone with an alkaline solution of sodium hypobromite at 35°–40° C., the aromatic acid is obtained by acidification and filtration. The products are purified by crystallisation from ethanol.

EXAMPLE 4

This example describes the preparation of trans-4-alkylcyclohexane-1-carboxylic acids by the following route:

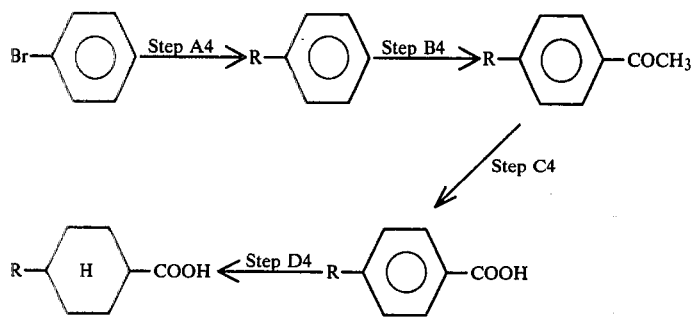

where R is an alkyl group-normal, branched or branched and chiral.

Certain alkylbenzenes, particularly n-alkylbenzes, are commercially available; otherwise they must be prepared from bromobenzene by step A4. The preparation of (+)-trans-4-(2'-methylbutyl)cyclohexane-1-carboxylic acid from bromobenzene by way of (+)-2-methylbutylbenzene will now be described by way of example.

Step A4

The production of (+)-2-methylbutylbenzene.

A solution of bromobenzene (0.51 mole) in sodium dried diethyl ether (200 ml) is added in drops to magnesium turnings (0.51 g atom) in sodium dried ether (50 ml). A single crystal of iodine is added to initiate the reaction, which is kept going by the addition of the bromobenzene. When addition is complete the solution is heated under reflux for 1 hr.

The solution of the Grignard reagent is then cooled in an ice bath and iron(III) chloride (0.0025 mole) in ether (2 ml) is added. A solution of (+)-2-methylbutyl bromide (0.54 mole) in sodium dried ether (100 ml) is then added over 30 min. The mixture is left to stir for 48 hrs at 25° C. The mixture is then poured into a 20% solution of hydrochloric acid in water, cooled to 0° C. and stirred for 30 min. The product is extracted into ether and the extracts washed with water and dried (Na$_2$SO$_4$). The ether is evaporated off and the oily residue distilled. The fraction of (+)-2-methylbutylbenzene boiling at 120° C. is collected at a pressure of 15 mm of mercury.

Step B4

The production of (+)-4-(2'-methylbutyl)acetophenone.

Crushed, anhydrous aluminium trichloride (0.295 mole) is suspended in dry carbon disulphide (80 ml). Acetyl chloride (0.25 mole) and (+)-2-methylbutylbenzene (0.23 mole), prepared in Step A4, are dissolved in dry carbon disulphide (80 ml) and added to the suspension of aluminium trichloride under anhydrous conditions. The mixture is then left to stir overnight. The solvent is distilled from the reaction mixture and the viscous residue poured onto crushed ice and stirred for 30 min. The product is extracted into ether, washed with water and dried (Na$_2$SO$_4$). The ether is removed by rotary evaporation and the oily residue distilled. The product boils at 95° C. at a pressure of 0.1 mm of mercury.

Step C4

The production of (+)-4-(2'-methylbutyl)benzoic acid.

A solution of sodium hypobromite prepared by dissolving bromine (156 g) in a solution of sodium hydroxide (3.5 mole) in water (700 ml) at 0° C. is added to a well stirred solution of (+)-4-(2'-methylbutyl) acetophenone (0.2 mole), mole), prepared in Step B4, in dioxan (500 ml). Throughout the addition, and for 15 minutes after the addition, the temperature is maintained at 35°–40° C. The excess of sodium hypobromite is destroyed by adding a solution of sodium metabisulphite. Water (3.5 L) is added and bromoform is distilled from the reaction mixture. On cooling, the solution is acidified with concentrated hydrochloric acid and the precipitated product is filtered off and washed with water. The product is crystallised from ethanol/water. The m.p. of the colourless crystals is 130° C.

Step D4

The production of (+)-trans-4-(2'-methylbutyl)cyclohexane-1-carboxylic acid.

A solution of (+)-4-(2'-methylbutyl)benzoic acid (0.2 mole) in sodium hydroxide (0.205 mole) dissolved in water (160 ml) is hydrogenated in the presence of Raney nickel catalyst (10 g) in an autoclave (1 l) at 195° C. and a pressure of hydrogen of 170 atm for 30 hrs. On cooling, the catalyst is filtered off and the filtrate washed with ether. The aqueous layer is separated and acidified. The precipitated acids are extracted into ether and the ether extracts are washed with water and then dried (Na$_2$SO$_4$). The ether is distilled off and the acids are dissolved in methanol (200 ml). The solution is treated successively with 40 g and 30 g of thiourea. After each treatment with thiourea the crystalline material formed is filtered off. The combined crystallisates are dissolved in a 5% solution (800 ml) of potassium hydroxide in water. This solution is acidified and the (+)-trans-4-(2'-methylbutyl)cyclohexane-1-carboxylic acid which precipitates out is extracted into ether. The ether extract is washed with water and dried (Na$_2$SO$_4$). The ether is evaporated off and the product is crystallised from acetone; the m.p. is 50.3° C.

Other members of this class of carboxylic acid can be prepared by analogous methods, which will be immediately apparant to those skilled in the art.

EXAMPLE 5

Preparation of (+)-4-(2'-methylbutyl)phenyl 2-chloro-4-hydroxybenzoate. This esterficiation may be carried out by the method described by Lowrance (Tet.

Lett. 1971, 3453). The reactants (2-chloro-4-hydroxybenzoic acid and (+)4-(2'-methylbutyl)phenol in equimolar amounts) are dissolved in toluene and heated in a Dean and Stark apparatus together with catalytic amounts of sulphuric acid and boric acid. After crystallisation from ethanol/water, the product has the m.p. 142° C.

The esters of the present invention are prepared by the route:

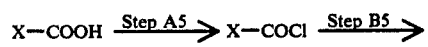

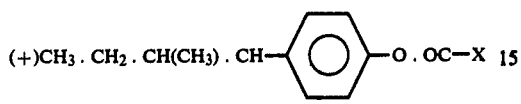

where X has the meanings specified hereinbefore and Example 6 is a typical esterification yielding a compound of the present invention.

EXAMPLE 6

Preparation of (+)-4-(2'-methylbutyl)phenyl 4-(2''-methylbutyl)biphenyl-4'-carboxylate.

Step A6

(+)-4-(2''-methylbutyl)biphenyl-4'-carboxylic acid (0.002 mole), prepared as mentioned earlier, is heated with thionyl chloride (20 ml) under anhydrous conditions for 1.5 hr. The excess of thionyl chloride is removed by distillation under reduced pressure. The acid chloride residue is used in the next step without further purification.

Step B6

(+)-4-(2''-methylbutyl)biphenyl-4'-carboxylic acid chloride (0.002 mole) prepared in Step A6, is dissolved in dry pyridine (10 ml) and cooled in an ice bath. (+)-4-(2'-methylbutyl)phenol (0.002 mole) is added to the stirred solution and the mixture is left for 18 hr to rise to room temperature. It is then heated at 100° C. for 1 hr. The pyridine is removed by rotary evaporation and the residue is purified by column chromatography using a silica gel column eluted with chloroform. The combined fractions of ester are crystallised from hexane or ethanol.

Using the general method disclosed in Example 6 above various esters were prepared and their physical properties are given in the Tables 1 to 7 below in which $R_c$ represents (+)—$CH_3.CH_2.CH(CH_3).CH_2$—

Where the property "pitch" is quoted in the tables below it has been determined by standard spectrophotometric procedures either on the pure sample or in admixture with Mixture A, the composition of which is quoted below.

| Mixture A | |
|---|---|
| Components | Composition (wt %) |
| 4-n-$C_5H_{11}$-4'-cyanobiphenyl | 43 |
| 4-n-$C_3H_7O$-4'-cyanobiphenyl | 17 |
| 4-n-$C_5H_{11}O$-4'-cyanobiphenyl | 13 |
| 4-n-$C_8H_{17}O$-4'-cyanobiphenyl | 17 |
| 4-n-$C_5H_{11}$-4''-cyano-p-terphenyl | 10 |

Where the test was carried out on a mixture the relative proportions are given in the relevant table.

TABLE 1

$R_c$—⟨○⟩—O.OC—⟨○⟩—⟨○⟩—R

| R | C-S (°C.) | $S_H$-$S_F$ (°C.) | $S_F$-$S_C$ (°C.) | $S_B/S_C$-$S_A$ (°C.) | $S_A$-Ch (°C.) | Ch-I (°C.) | Pitch (μm) |
|---|---|---|---|---|---|---|---|
| n-$C_5H_{11}$ | 66.0 | — | — | 77.3 | 133.9 | 156 | 0.23 |
| n-$C_6H_{13}$ | 81.0 | — | — | (71.0) | 132.6 | 146.2 | 0.23 |
| n-$C_7H_{15}$ | 74.6 | — | — | 75.0 | 138.4 | 144.6 | 0.23 |
| n-$C_8H_{17}$ | 55 | 65.8 | 71.2 | 84.2 | 136.2 | 141.3 | 023 |

TABLE 2

$R_c$—⟨○⟩—O.OC—⟨○⟩—⟨○⟩—OR

| R | C-$S_F$ (°C.) | $S_F$-$S_C$ (°C.) | $S_C$-$S_A$ (°C.) | $S_A$-Ch (°C.) | $S_A$/$Ch$-I (°C.) | Pitch (μm) |
|---|---|---|---|---|---|---|
| n-$C_8$—$H_{17}$ | 78.0 | — | 128.2 | 171.0 | 174.2 | 0.23 |
| n-$C_9H_{19}$ | 72.0 | 77.6 | 132.0 | 168.0 | 170.0 | 0.23 |
| n-$C_{12}H_{25}$ | 76.7 | 77.2 | 132.0 | — | 161.2 | 0.23 |

TABLE 3

$R_c$—⟨○⟩—O.OC—⟨○⟩—OR

| R | C-$S_A$/I (°C.) | $S_A$-Ch (°C.) | Ch-I (°C.) | Pitch (μm) |
|---|---|---|---|---|
| n-$C_6H_{13}$ | 38.0 | — | (36.7) | 0.23 |
| n-$C_7H_{15}$ | 45.5 | — | (36.3) | 0.23 |
| n-$C_8H_{17}$ | 47.5 | — | (42.0) | 0.23 |
| n-$C_9H_{19}$ | 49.5 | (37.2) | (42.7) | 0.23 |
| n-$C_{10}H_{21}$ | 41.8 | 42.2 | 45.3 | 0.23 |

TABLE 4

$R_c$—⟨○⟩—O.OC—⟨○⟩—R

| R | C-I (°C.) | Ch-I* (°C.) | Pitch (μm) |
|---|---|---|---|
| n-$C_5H_{11}$ | 5–6 | (−1) | 0.23 |

*Virtual Ch-I temperature.

TABLE 5

$R_c$—⟨○⟩—O.OC—⟨H⟩—R

| R | C-I (°C.) | Ch-I* (°C.) | Pitch** (μm) |
|---|---|---|---|
| $C_2H_5$ | 2.0 | (−33) | 2.0 |
| n-$C_3H_7$ | 24.0 | (1) | 2.0 |
| n-$C_4H_9$ | 22.0 | (−14) | 2.0 |
| n-$C_5H_{11}$ | 17.0 | (7) | 2.0 |

*Virtual Ch-I temperature.
**Measured using a 12 wt % solution in Mixture A.

The remaining tables all relate to compounds having chiral groups at both ends of the molecule.

TABLE 6

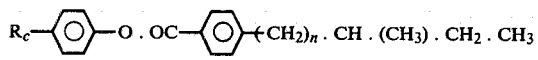

where n=1, the compound is an oil—virtual Ch-I, −53° C.

The pitch of an 8 wt % solution in Mixture A is 1.1 μm.

TABLE 7

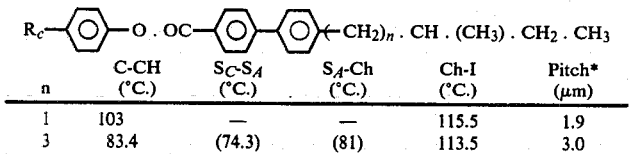

| n | C-CH (°C.) | S$_C$-S$_A$ (°C.) | S$_A$-Ch (°C.) | Ch-I (°C.) | Pitch* (μm) |
|---|---|---|---|---|---|
| 1 | 103 | — | — | 115.5 | 1.9 |
| 3 | 83.4 | (74.3) | (81) | 113.5 | 3.0 |

*The pitch is measured using a 5% by weight concentration in Mixture A.

TABLE 8

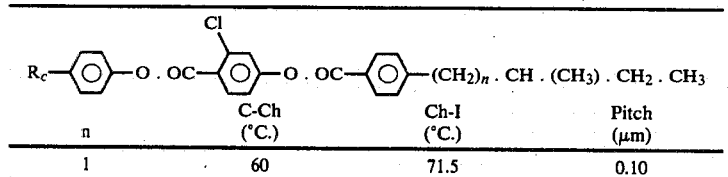

| n | C-Ch (°C.) | Ch-I (°C.) | Pitch (μm) |
|---|---|---|---|
| 1 | 60 | 71.5 | 0.10 |

TABLE 9

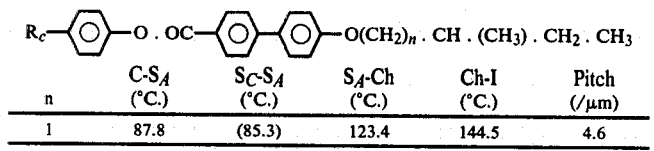

| n | C-S$_A$ (°C.) | S$_C$-S$_A$ (°C.) | S$_A$-Ch (°C.) | Ch-I (°C.) | Pitch (/μm) |
|---|---|---|---|---|---|
| 1 | 87.8 | (85.3) | 123.4 | 144.5 | 4.6 |

*Pitch measured for a 10% by weight solution in Mixture A.

It should be noted at this point that where chirality in a molecule results from an optically active alkyl or alkyloxy group which has its point of asymmetry at an odd number of atoms from the ring system and the absolute configuration at the asymmetric centre is S, then the cholesteric helix is laevo. Conversely, when the asymmetric centre (S) is at an even number of atoms from the ring system then the cholesterics are dextro in type.

Thus when a molecule contains two chiral centres which promote cholesteric helices of the same type as defined above, then the pitch length of the resulting material is less than that of the analogous material with one chiral centre. Conversely if the two chiral centres promote cholesteric helices of opposite types as described above, then the material will have a greater pitch length than the analogous material with only one chiral centre.

The pure materials detailed in Tables 1 to 9 above are of particular interest when used as mixtures (solutions) with one another or with other compatible liquid crystal forming materials, advantageously the 4-n-alkyl and 4-n-alkyloxy-4'-cyanobiphenyls and related derivatives of p-terphenyl.

PHASE CHANGE MIXTURES

The following mixtures are examples of possible phase-change cholesterics.

| MIXTURE 1 | |
|---|---|
| Components | Composition % by weight |
| Mixture A | 88 |
| R$_c$—⟨O⟩—O.OC—⟨O⟩—CH$_2$.CH.(CH$_3$).CH$_2$CH$_3$ | 12 |
| Pitch = 0.7 /μm; Ch-I 57° C. | |

| MIXTURE 2 | |
|---|---|
| Components | Composition % by weight |
| Mixture A | 92 |
| R$_c$—⟨O⟩—O.OC—⟨O⟩—CH$_2$.CH.(CH$_3$).CH$_2$CH$_3$ | 8 |
| Pitch = 1.1 /μm; Ch-I 62° C. | |

MIXTURE 3

| Components | Composition % by weight |
|---|---|
| Mixture A | 91 |
| $R_c$—⟨O⟩—O.OC—⟨O⟩—$CH_2.CH.(CH_3).CH_2.CH_3$ | 5 |
| $R_c$—⟨O⟩—O.OC(—⟨O⟩—)$_2$$CH_2.CH.(CH_3).CH_2CH_3$ | 4 |
| Pitch = 1.0 / 82 m; Ch-I 67.4° C. | |

THERMOCHROMIC MIXTURE

The following mixtures are examples of possible thermochromic compositions incorporating the afore-mentioned esters.

MIXTURE 4

| Components | Composition % by weight | |
|---|---|---|
| $n$-$C_8H_{17}$—⟨O⟩—⟨O⟩—CN | 52 | |
| $R_c$—⟨O⟩—O.OC—⟨O⟩—⟨O⟩—$R_c$ | 19 | $S_A$-Ch, 21° C. |
| $R_c$—⟨O⟩—O.OC—⟨H⟩—$C_4H_9$-$n$ | 26 | Ch-I, 44.8° C. |
| $R_c$—⟨O⟩—O.OC—⟨O⟩—⟨O⟩—$OC_{12}H_{25}$-$n$ | 3 | |

| Selective Reflection | Temp (°C.) |
|---|---|
| Red | 26 |
| Yellow | 31 |
| Green | 33 |
| Turquoise | 41 |
| Blue | 43 |

MIXTURE 5

| Components | Composition % by weight | |
|---|---|---|
| $R_c$—⟨O⟩—O.OC—⟨O⟩—O.$n$-$C_6H_{13}$ | 59 | |
| $R_c$—⟨O⟩—O.OC—⟨O⟩—O.$n$-$C_8H_{17}$ | 18 | $S_A$-Ch, 24.5° C. |
| $R_c$—⟨O⟩—O.OC—⟨O⟩—O.$n$-$C_{10}H_{21}$ | 23 | Ch-I, 39° C. |

| Selective Reflection | Temp (°C.) |
|---|---|
| Red | 24.5 |
| Yellow | 24.6 |
| Green | 24.7 |
| Turquoise | 24.9 |
| Blue | 25.2 |

MIXTURE 6

| Components | Composition % by weight | |
|---|---|---|
| $n$-$C_8H_{17}$—⟨O⟩—⟨O⟩—CN | 45 | |
| $n$-$C_{10}H_{21}$—⟨O⟩—⟨O⟩—CN | 21 | $S_A$-Ch, 18.5° C. |
| $R_c$—⟨O⟩—O.CO—⟨O⟩—$R_c$ | 14 | Ch-I, 43.0° C. |
| $R_c$—⟨O⟩—O.OC—⟨O⟩—⟨O⟩—$R_c$ | 20 | |

| Selective Reflection | Temperature °C. |
|---|---|
| Red | 23.5 |
| Yellow | 25.5 |

-continued

| MIXTURE 6 | |
|---|---|
| Green | 26.6 |
| Turquoise | 33.0 |
| Blue | 35.0 |

Although none of the above disclosed mixture is believed to be as eutectic, no separation of any component has been observed over several months.

We claim:

1. A liquid crystal compound which is an optically active ester having the formula:

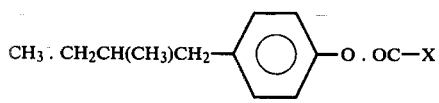

wherein X is

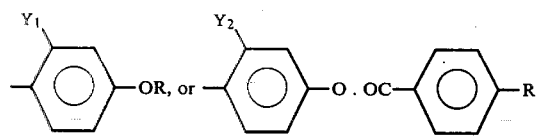

R is an alkyl group, which may be chiral, having less than 15 carbon atoms, $Y_1$ is halogen or methyl and $Y_2$ is halogen or methyl.

2. A liquid crystal compound as claimed in claim 1 and wherein X is:

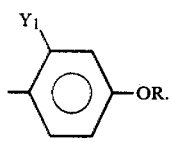

3. A liquid crystal compound as claimed in claim 1 and wherein X is:

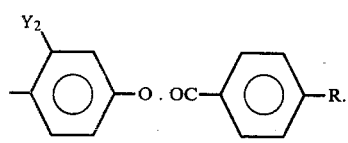

4. A liquid crystal compound as claimed in claim 3 and wherein $Y_2$ is chlorine and R is 2-methylbutyl.

5. A liquid crystal compound as claimed in claim 1 and which is prepared by reacting on optically active substituted phenol compound having the formula:

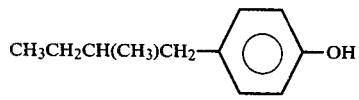

with an acid chloride having the formula X-COCl where X is as defined in claim 1 has the same meaning as R in claim 1.

6. A liquid crystal compound as claimed in claim 5 and wherein the optically active substituted phenol compound is prepared by hydrolyzing a corresponding methoxy compound:

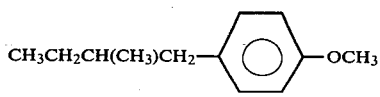

has the same meaning as R* in claim 5; said methoxy compound being prepared by the reaction of

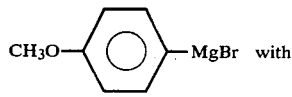

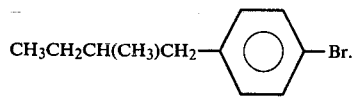

7. A liquid crystal compound as claimed in claim 3 and which is prepared by reacting an optically active hydroxy benzoate compound having the formula

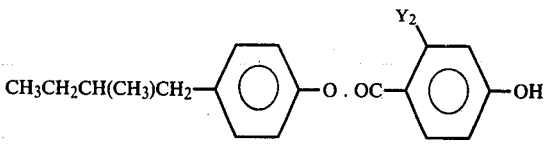

with an acid chloride having the formula X-COCl where X is

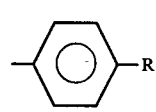

8. A liquid crystal compound as claimed in claim 7 and wherein said hydroxy benzoate compound is prepared by reacting a compound

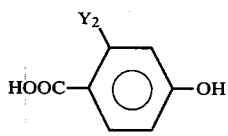

with an optically active compound

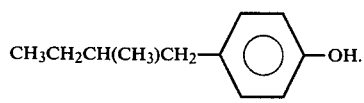

9. A liquid crystal material which comprises a mixture of at least two compounds as claimed in claim 1, said mixture exhibiting a cholesteric mesophase suitable for use in a cholesteric-to-mesophase change electro-optic device.

10. A liquid crystal material which comprises a mixture of at least one compound as claimed in claim 1 together with at least one compound selected from a 4'-alkyl-4-cyanobiphenyl, a 4'-alkoxy-4-cyanobiphenyl and a 4''-alkyl-4-cyano-p-terphenyl, said mixture exhibiting a cholesteric mesophase suitable for use in a cholesteric-to-mesophase change electro-optic device.

11. A liquid crystal material which contains at least one compound as claimed in claim 1, said material being in the form of a thin film in the Grandjean plane texture.

12. In a liquid crystal device including means for containing a region of liquid crystal material, a region of liquid crystal material in said containing means, and means for applying an electrical field to said material to alter the molecular arrangement in said material, the improvement wherein said containing means contains a liquid crystal material of the formula of claim 1.

* * * * *